US012691015B2

(12) United States Patent
Picot

(10) Patent No.: US 12,691,015 B2
(45) Date of Patent: Jul. 28, 2026

(54) RETAINING DEVICE, ABSORBENT ITEM COMPRISING SUCH A DEVICE, AND METHOD FOR MANUFACTURING SUCH A DEVICE

(71) Applicant: APLIX, Le Cellier (FR)

(72) Inventor: Lionel Picot, Le Cellier (FR)

(73) Assignee: APLIX, Le Cellier (FR)

( * ) Notice: Subject to any disclaimer, the term of this patent is extended or adjusted under 35 U.S.C. 154(b) by 579 days.

(21) Appl. No.: 18/006,844

(22) PCT Filed: Jul. 12, 2021

(86) PCT No.: PCT/FR2021/051295
§ 371 (c)(1),
(2) Date: Jan. 25, 2023

(87) PCT Pub. No.: WO2022/029378
PCT Pub. Date: Feb. 10, 2022

(65) Prior Publication Data
US 2023/0329928 A1 Oct. 19, 2023

(30) Foreign Application Priority Data
Aug. 3, 2020 (FR) ...................................... 2008241

(51) Int. Cl.
*A61F 13/62* (2006.01)
*B29C 48/07* (2019.01)
(Continued)

(52) U.S. Cl.
CPC ............ *A61F 13/625* (2013.01); *B29C 48/07* (2019.02); *B29L 2031/4878* (2013.01); *B29L 2031/729* (2013.01)

(58) Field of Classification Search
CPC ....... A61F 13/625; B29C 48/07; B29C 41/28; B29C 43/222; B29C 43/46; B29C 43/48;
(Continued)

(56) References Cited

U.S. PATENT DOCUMENTS 3,147,528 A * 9/1964 Erb ................... B29C 45/14778
428/100
3,312,583 A 4/1967 Rochlis
(Continued)

FOREIGN PATENT DOCUMENTS

CN 1513395 A 7/2004
CN 109070407 A 12/2018
(Continued)

OTHER PUBLICATIONS

Notice of Reasons for Refusal issued in corresponding application No. JP 2023-504843, mailed Jan. 7, 2025.
(Continued)

*Primary Examiner* — Rebecca E Eisenberg
*Assistant Examiner* — Brandon W. Levy
(74) *Attorney, Agent, or Firm* — Bookoff McAndrews, PLLC

(57) ABSTRACT

Retainer device comprising a base extending along a longitudinal direction and a plurality of retainer elements extending from the upper face of the base, each retainer element having a value according to a first geometric dimension. The retainer device has at least two retainer zones and an intermediate zone disposed between the two retainer zones and connecting the two retainer zones, the retainer elements disposed in the first and second retainer zones having values according to the first geometric dimension which are greater than the values according to the first geometric dimension of the retainer elements disposed in the intermediate zone.

19 Claims, 5 Drawing Sheets

(51) Int. Cl.
  *B29L 31/00*          (2006.01)
  *B29L 31/48*          (2006.01)

(58) Field of Classification Search
  CPC ... B29C 43/50; B29C 43/52; B29C 2043/465;
        B29L 2031/4878; B29L 2031/729; B29K
        2023/00; A44B 18/0049; A44B 18/0065;
        A44B 18/0061; A44B 18/0088; A44B
        18/0003; A44B 18/00; Y10S 128/15
  See application file for complete search history.

(56)                References Cited

U.S. PATENT DOCUMENTS

| | | | | |
|---|---|---|---|---|
| 5,657,517 | A * | 8/1997 | Akeno | A44B 18/0061 |
| | | | | 24/442 |
| 5,692,271 | A * | 12/1997 | Provost | A61F 13/625 |
| | | | | 24/442 |
| 5,884,374 | A | 3/1999 | Clune | |
| 5,933,927 | A * | 8/1999 | Miller | A44B 18/0088 |
| | | | | 24/452 |
| 6,206,679 | B1 | 3/2001 | Provost et al. | |
| 6,276,032 | B1 * | 8/2001 | Nortman | A61F 13/622 |
| | | | | 24/572.1 |
| 6,588,073 | B1 * | 7/2003 | Zoromski | A61F 13/622 |
| | | | | 24/446 |
| 2002/0116799 | A1 * | 8/2002 | Martin | A61F 13/625 |
| | | | | 24/452 |
| 2004/0194262 | A1 * | 10/2004 | Kurtz, Jr. | A44B 18/0061 |
| | | | | 24/452 |
| 2005/0060849 | A1 * | 3/2005 | Vanbenschoten | A61F 13/625 |
| | | | | 24/451 |
| 2013/0067701 | A1 * | 3/2013 | Grady | B29C 43/28 |
| | | | | 427/256 |

FOREIGN PATENT DOCUMENTS

| | | | |
|---|---|---|---|
| DE | 10085304 | T1 | 12/2002 |
| EP | 1702599 | A1 | 9/2006 |
| FR | 3050624 | A1 | 11/2017 |
| FR | 3104387 | A1 | 6/2021 |
| JP | H08174693 | A | 7/1996 |
| JP | H11509106 | A | 8/1999 |
| JP | 2000139520 | A | 5/2000 |
| JP | 2001510058 | A | 7/2001 |
| JP | 2005319142 | A | 11/2005 |
| JP | 2013518747 | A | 5/2013 |
| JP | 2013212211 | A | 10/2013 |
| JP | 2013212214 | A | 10/2013 |
| JP | 2017533013 | A | 11/2017 |
| WO | 2017187097 | A1 | 11/2017 |
| WO | WO-2019082103 | A1 * | 5/2019 ......... A44B 18/0065 |

OTHER PUBLICATIONS

Search Report issued in corresponding application No. JP 2023-504843, mailed Dec. 23, 2024.
International Search Report issued in International Application No. PCT/FR2021/051295, on Oct. 26, 2021, with English Translation (5 pages).

* cited by examiner

[Fig. 1]
[Fig. 2]
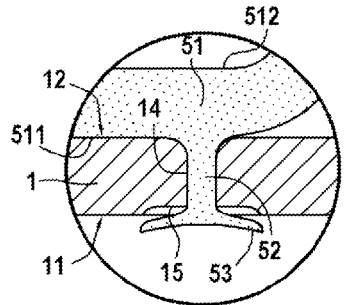

[Fig. 3]
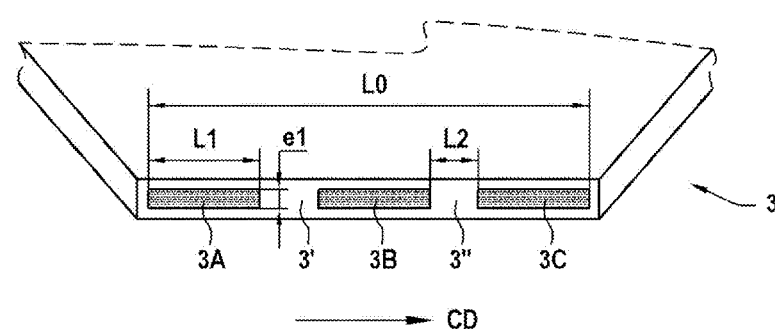
[Fig. 4]
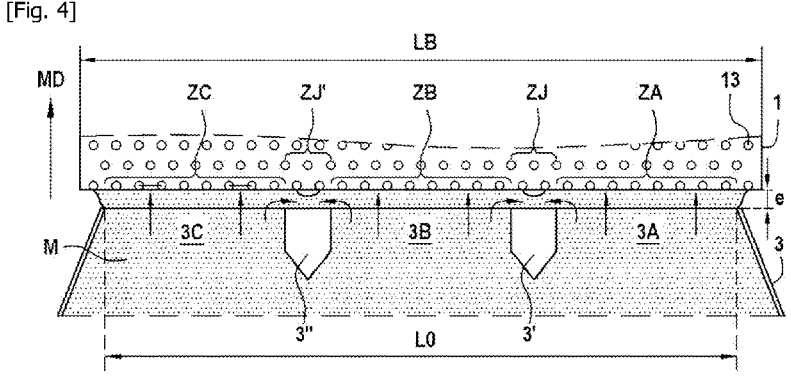
[Fig. 5]
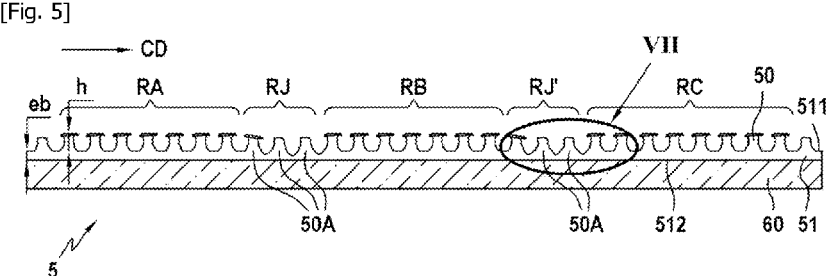

[Fig. 6]
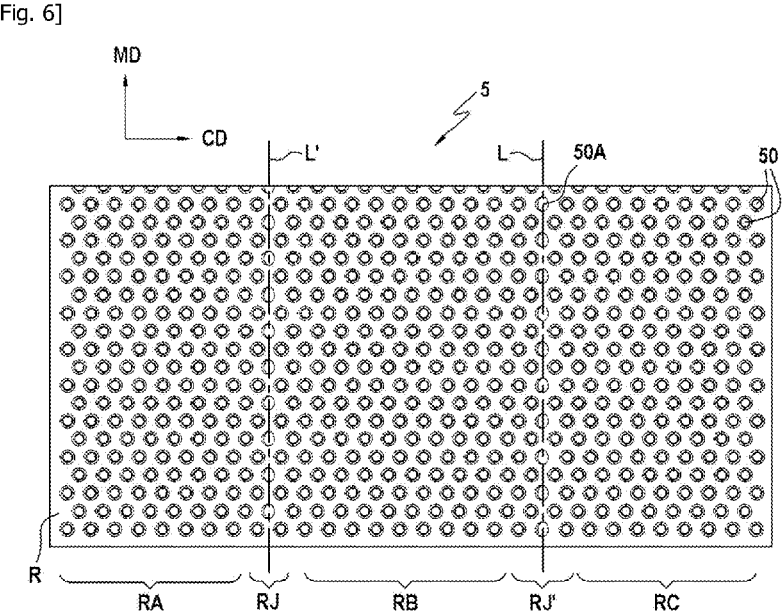
[Fig. 7]
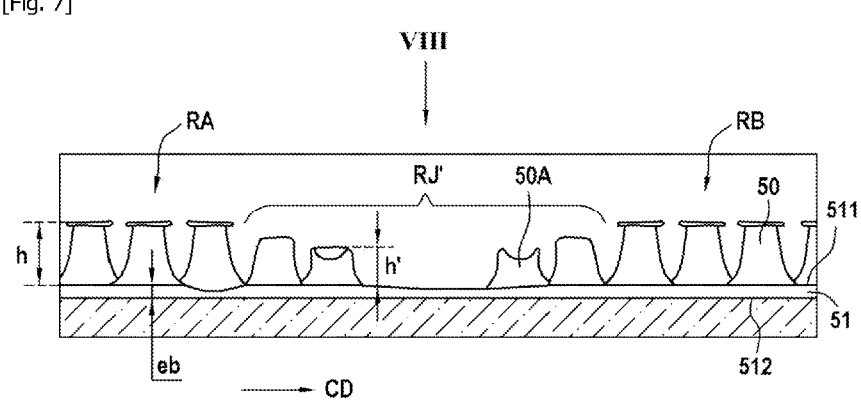

[Fig. 8]
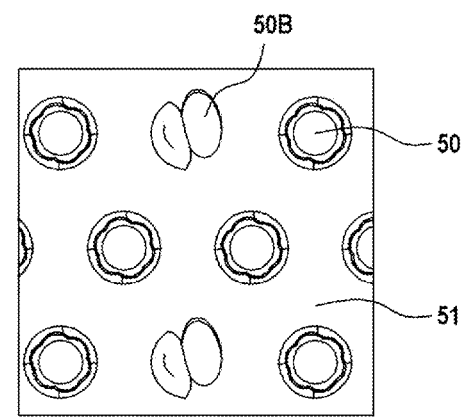
[Fig. 9]
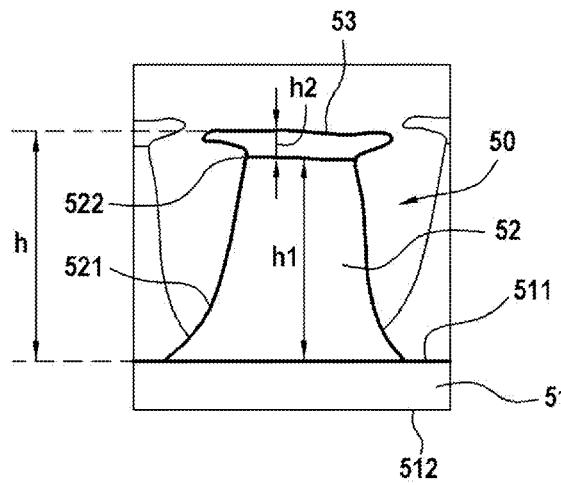

[Fig. 10]
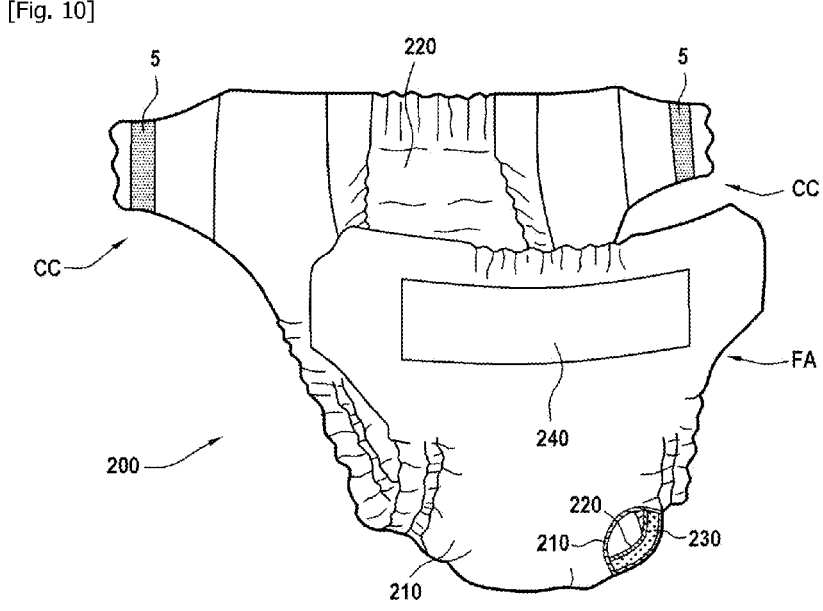

RETAINING DEVICE, ABSORBENT ITEM COMPRISING SUCH A DEVICE, AND METHOD FOR MANUFACTURING SUCH A DEVICE

CROSS-REFERENCE TO RELATED APPLICATION(S)

This patent application is the U.S. national stage entry of International Application No. PCT/FR2021/051295, filed on Jul. 12, 2021, which claims priority to French Application No. 2008241, filed on Aug. 3, 2020.

TECHNICAL FIELD

The present disclosure relates to the field of retainer systems, particularly closing or anti-slip systems. The disclosure more particularly relates to the retainer systems with retainer elements, particularly to the hook-and-loop retainer systems, whose retainer elements can be retained in loops or the like.

The disclosure also relates to the field of associated manufacturing methods and equipment.

The disclosure also relates to the field of absorbent items of the baby diaper or adult incontinence diaper type comprising a hook-and-loop retainer system for the diaper.

PRIOR ART

The retainer systems comprising retainer elements carried by a base are well known and used in many fields of application, leading actually to the production of multiple forms of retainer elements, particularly hooks, intended to cooperate mutually or with complementary elements such as loops.

A recurring problem with such products relates to the applied retainer force, in particular given the greatly reduced dimensions of the associated retainer elements and manufacturing constraints.

Indeed, the production of hooks with high strengths naturally leads to oversizing, which affects the softness of the system and therefore the experience of the user, which is highly detrimental in some fields, in particular in the field of hygiene, and also leads to an increased consumption of material which is detrimental in terms of cost, and also detrimental in terms of manufacture insofar as the production of bulky parts leads to increased material cooling times, actually increasing the production line occupancy time.

Document WO2017187097 discloses a retainer device comprising retainer elements carried by a base and having particular dimensional and geometric characteristics.

The present disclosure thus aims to address these various problems by further improving the known devices.

Presentation of the Disclosure

According to a first aspect, the disclosure relates to a retainer device, comprising:
- a base extending along a longitudinal direction and having an upper face and a lower face,
- a plurality of retainer elements extending from the upper face of the base, each retainer element having a value according to a first geometric dimension, the retainer device having at least two retainer zones and an intermediate zone disposed between the two retainer zones and connecting the two retainer zones, the retainer elements disposed in the first and second retainer zones having values according to the first geometric dimension which are greater than the values according to the first geometric dimension of the retainer elements disposed in the intermediate zone.

Optionally, the retainer zones and the intermediate zone form elongated zones in the form of tapes in a common tape, the elongated zones and the common tape being optionally elongated along the longitudinal direction.

Optionally, the intermediate zone has at least one part in which the base has a thickness smaller than a thickness of the base in the retainer zones.

Optionally in the intermediate zone, the base has a weld line.

Optionally, in the intermediate zone, the base has voids.

Optionally in the intermediate zone, the base has a state of material different from the state of material it has in the retainer zones.

Optionally, in the retainer zones, the retainer elements have a value according to the first geometric dimension which is substantially constant.

Optionally, considered in the direction going from the first retainer zone to the second retainer zone, the intermediate zone has successive retainer elements whose value according to the first geometric dimension decreases then retainer elements whose value according to the first geometric dimension increases.

Optionally, the values according to the first geometric dimension are measured according to a sectional view perpendicular to the base, particularly a sectional view perpendicular to the base and parallel to the cross direction.

Optionally, the values according to the first geometric dimension are measured according to a view parallel to the base and at a distance from the retainer elements.

Optionally, any straight line passing through at least one retainer element and extending along the direction going from the first retainer zone to the second retainer zone while passing through said first and second retainer zones, intersects at least 3 retainer elements particularly at least 5 retainer elements in each of the first and second retainer zones.

Optionally, any straight line passing through at least one retainer element and extending along the direction going from the first retainer zone to the second retainer zone while passing through said first and second retainer zones, intersects at least 1 retainer element, particularly at least 2 retainer elements in the intermediate zone. It can be provided that for any straight line of the type defined above intersects up to 70 retainer elements, even 100 retainer elements in each of the first and second retainer zones and, optionally, up to 10 retainer elements, or even up to 30 retainer elements in the intermediate zone.

Optionally, the first geometric dimension is the height of the retainer elements, measured, for each retainer element, between a lower end of the retainer element connected to the base and an upper end of the retainer element opposite to the lower end.

Optionally, at least in the retainer zones, the retainer elements are each formed of a rod surmounted by a head protruding from the rod, at least part of the retainer elements of the intermediate zone being optionally devoid of a head.

Optionally, at least in the retainer zones, the retainer elements are distributed in a regular and repeating pattern.

Optionally, the retainer elements are evenly distributed, for example in the form of rows or columns or in a staggered manner.

Optionally, the device further comprises a substrate carrying the base, the substrate optionally comprising a layer of non-woven material.

Optionally, the assembly formed by the base and the retainer elements has a basis weight comprised between 10 and 120 g/m$^2$ (grams per square meter), particularly between 30 and 80 g/m$^2$, in some cases between 30 and 70 g/m$^2$, more particularly between 50 and 70 g/m$^2$. When the device comprises a substrate, these basis weight values are particularly verified for the assembly comprising the base and the retainer elements, without the substrate.

Particularly, the base and the retainer elements are present in the retainer zones and in the intermediate zone.

Particularly, the intermediate zone connects the two retainer zones contiguously, with no space between the intermediate zone and, respectively, each of the two retainer zones.

Particularly, the first geometric dimension is a dimension along a given direction. As mentioned, this is for example the height of the retainer elements.

It can however be a dimension other than the height, for example a cross dimension of the retainer elements, measured parallel to the plane of the base.

When the retainer elements have, at least in some portions, a symmetry of revolution, the first geometric dimension can be a diametrical dimension of these portions. Of course, these dimensions can be combined. Thus, in addition to the first geometric dimension, the retainer elements can have a second geometric dimension for which it is verified that the retainer elements disposed in the first and second retainer zones have values according to the second geometric dimension which are greater than the values according to the second geometric dimension of the retainer elements disposed in the intermediate zone.

In the intermediate zone, the retainer elements have geometric characteristics which are degraded relative to the same characteristics of the retainer elements of the retainer zones so that, at least for the first geometric dimension, the retainer elements of the intermediate zone have lower values than those of the retainer zones.

However, to some extent, the retainer elements of the intermediate zone can contribute to the retainer force. They allow having fully effective retainer elements over the large zones that the retainer zones constitute, without interruption between these fully effective zones whereas, due to their reduced values for the first geometric dimension, the retainer elements of the retainer zone represent lesser masses than those of the retainer elements of the retainer zones, which allows producing an effective retainer device, of low basis weight.

The retainer device has increased flexibility in the intermediate zone(s) relative to the retainer zones. For an equal number of retainer elements, the device is therefore not only lighter but also more flexible than a device in which all the retainer elements would be non-degraded (that is to say they would all be like two of the retainer zones). This increased flexibility promotes the quality of the retention by allowing for example the device to better follow the movements of the person wearing an item equipped with such a retainer device.

Particularly, in each retainer zone, the value of the first geometric dimension of the retainer elements varies within a determined range relative to a maximum value, by being for example comprised between 80% and 100% of the maximum value, even between 85% and 100% of the maximum value, or even between 90% and 100% of this maximum value.

Particularly, the maximum value of the first geometric dimension can be substantially the same for the two retainer zones, which means that this maximum value is the same for the two retainer zones with a tolerance of the order of 10% or even 5%.

Hereinafter, the "maximum reference value" for the first geometric dimension is the greater of the two maximum values of the first geometric dimension respectively observed for each of the two retainer zones. As indicated, these two maximum values are normally close, so that the reference maximum value is itself close to each of these two maximum values.

On the other hand, in the intermediate zone, the value of the first geometric dimension can be considerably lower. Thus, for at least part of the retainer elements of the intermediate zone, the value of the first geometric dimension can be less than or equal to 30% of the maximum reference value, or less than or equal to 50% of the maximum reference value, or less than or equal to 60% of the maximum reference value. Here, "at least part of the retainer elements of the intermediate zone" means at least one retainer element, or at least 10% or at least 20% or at least 40% of the retainer elements of the intermediate zone. However, at least part of the retainer elements of the intermediate zone can have substantial values for the first geometric dimension. Thus, at least part of the retainer elements of the intermediate zone can have a value for the first geometric dimension of the order of at least 5%, or at least 10%, or at least 20% of the maximum reference value. Here, "at least part of the retainer elements of the intermediate zone" means at least one retainer element, or at least 10% or at least 20% or at least 40% of the retainer elements of the intermediate zone.

According to a second aspect, the disclosure relates to an absorbent item of the baby diaper or adult incontinence diaper type, the item comprising an assembly which comprises two external sheets and an absorbent core disposed between the external sheets, the assembly being arranged so as to present a first face of the diaper, particularly a front face, and sides of the diaper, the item comprising a hook-and-loop retainer system comprising receiving loops carried by one of the elements among the first face of the diaper and one of the sides of the diaper, and at least one retainer device according to the disclosure, carried by the other of the elements among the first face of the diaper and said one of the sides of the diaper, so that the retainer elements cooperate with the receiving loops when said at least one of the sides of the diaper is placed against the first face of the diaper to retain said at least one of the sides of the diaper with respect to said first face.

The first face of the diaper can be particularly the front face of the diaper, that is to say the outer face located on the side of the lower abdomen of the person wearing it. The sides of the diaper can be lateral panels of the diaper or lugs, particularly elastic lugs.

By "retaining said at least one of the sides of the diaper with respect to said first face", it is meant closing this side of the diaper against the first face by thus retaining them together to prevent them from separating, and/or retaining this side of the diaper against the first face by avoiding or at least limiting their relative slippage.

Optionally, the retainer device can be arranged on a surface comprising loops, for example on a region of the comfort strip (generally designated by landing zone), for example near the lateral borders of the comfort strip.

According to a third aspect, the disclosure relates to a method for manufacturing a retainer device, in which:

a molding device is provided having a plurality of cavities formed in a recessed manner from a surface, the molding device being optionally a molding strip, a heated molding material is applied on said surface, using an applicator by allowing the molding material to penetrate into the cavities to form retainer elements, method according to which are generated two separate adjacent flows of a molding material applied on the surface in two application zones by causing the molding material to flow so that the two flows meet in a junction zone so as to form a base, so that the material penetrates further into the cavities present in the application zones than into the cavities present in the junction zone.

Here, "two adjacent flows" means "at least two adjacent flows". It is particularly possible to have three adjacent flows two by two, and two junction zones, each between two adjacent flows.

Optionally, the applicator is an extrusion device comprising two adjacent channels separated by a partition, and the molding material is applied by moving the molding device and the extrusion device relative to each other in a longitudinal direction.

Optionally, the channels can be of identical sections, the section of a channel being considered transversely to the direction of progress of the material in the channel, that is to say being normally considered along the direction CD.

There can be more than two channels, separated two by two by respective partitions, which can be optionally identical.

Optionally, the channels can be of different sections.

Optionally, the partitions can have different geometric characteristics.

Particularly when the number of channels is greater than or equal to 3, it is conceivable that the channels located outside in the direction CD have sections different from, particularly lower than, the channels located inside.

Optionally, the channels and the partition(s) that separate them can be disposed symmetrically relative to a plane of symmetry, which is particularly a plane defined by the direction MD and a direction perpendicular to the plane defined by the directions MD and CD, this plane of symmetry passing particularly through the middle of the width of the applicator.

Optionally, before cooling of the molding material, a substrate is applied against the plastic material applied on the surface of the molding device, so that said material is sandwiched between the surface of the molding device and the substrate.

Of course, it can be provided to bring the same molding material, or on the contrary different materials, into the different channels.

Particularly, the cavities of the molding device which serve to form the retainer elements may all be analogous.

Particularly, the cavities of the molding device which serve to form the retainer elements can be distributed homogeneously in the molding device (more specifically, in the surface of the molding device which is intended to receive the molding material). In this case, these cavities are present in the application zones and in the junction zone according to the same distribution or density. Due to the creeping mobilizing the material in the junction zone, this material presents less facility to penetrate into the cavities present in the junction zone than into the cavities present in the application zones, so that retainer elements coming from the cavities present in the junction zone are degraded compared to those coming from the cavities present in the application zones. The application zones therefore serve to form retainer zones of the retainer device, while the junction zone is used to form an intermediate zone.

Due to the creeping in the junction zone, the material can be present in this zone with a thinner thickness than in the application zones so that, in its part coming from the junction zone, the base of the retainer device can have a lower thickness in its parts coming from the application zones.

BRIEF DESCRIPTION OF THE DRAWINGS

Other characteristics and advantages of the object of present disclosure will emerge from the following description of one embodiment, given by way of non-limiting example, with reference to the appended drawings.

FIG. 1 schematically represents equipment for the production of a retainer device with retainer elements.

FIG. 2 is an enlargement of the zone II of FIG. 1.

FIG. 3 is a schematic sectional view along the line III-III of FIG. 1.

FIG. 4 is a schematic partial view according to the arrow IV and the line IV-IV of FIG. 1.

FIG. 5 shows, in cross section, an item comprising a retainer device according to the present disclosure.

FIG. 6 is a top view of the item of FIG. 5.

FIG. 7 is an enlarged view of the detail VII of FIG. 5.

FIG. 8 is a partial view according to the arrow VIII of FIG. 7.

FIG. 9 is a detail of a retainer element of the retainer device according to the present disclosure.

FIG. 10 shows an absorbent item comprising a retainer device according to the disclosure.

DETAILED DESCRIPTION

FIG. 1 schematically shows an example of equipment for the production of a retainer device with retainer elements.

The equipment as represented comprises a molding strip 1 positioned on rotational drive means 2 comprising here two rolls 21 and 22, and a material distribution means or applicator 3 adapted to apply a molding material, for example plastic and/or elastic molding material, on a surface of the molding device.

The molding strip 1 is an example of a molding device.

The equipment serves to manufacture a retainer device 5, which is demolded from the molding device using a roll 6.

The example illustrated is in this case of the type described in document WO2017187097; it can be in particular modified or supplemented as indicated in this document or in document FR 1914162. The illustrated example comprising two rolls 21, 22 is not limiting, the number and the arrangement of the roll(s) can vary in particular in order to adapt to the length of the molding strip 1 and to the different positions of the equipment. It could be for example possible to use three rolls or just one so that the molding strip is arranged on the periphery of the single roll to form a sleeve or a screen. Particularly, only one of the two rolls can be driven in rotation by motorized means, for example the roll 21, the other roll 22 being free, that is to say without motorized means, and driven in rotation via the molding strip, itself driven by the roll 21.

A longitudinal direction is defined relative to the direction of progress of the molding strip 1. This longitudinal direction is commonly referred to as "machine direction" or MD. The longitudinal direction is designated by the axis MD in the figures.

A "cross direction" or CD is also defined, corresponding to a direction perpendicular to the longitudinal direction, and extending parallel to the inner and outer faces of the molding strip. The cross direction is designated by the axis CD in the figures.

The molding strip 1 as presented comprises an inner face 11 and an outer face 12, the inner face 11 being in contact with the rotational drive means 2, while the outer face has the surface on which the molding material is applied by the applicator 3.

More specifically, the applicator 3 is disposed facing the molding strip 1, by being spaced from the molding strip 1 so as to define an air gap e indicated in FIG. 1. The reference A marks the limit of the material injected on the outer face 12 of the molding strip 1, corresponding to the rear front of the material injected on the molding strip 1 relative to the direction of displacement of the molding strip 1.

As can also be seen in FIGS. 1 and 4, the molding strip 1 is provided with a plurality of cavities 13 allowing the production of retainer elements of the retainer device 5.

In this case, the cavities 13 represented in FIG. 1 are each formed so as to serve for the production of retainer elements of the hook type. Thus, as can be seen better in FIG. 2, each cavity defines a rod 14 extending from the outer face 12 towards the inner face 11 of the molding strip 1 and a head 15 extending between the rod 14 and the inner face 11 of the molding strip 1. In the example illustrated, the heads 15 of the cavities 13 open out onto the inner face 11 of the molding strip 1. The cavities 13 are therefore through cavities. Such an embodiment is not limiting, the cavities 13 can also be blind, and therefore not emerge from the inner face 11 of the molding strip 1. In addition, the cavities can be of different shapes, in particular by being devoid of heads.

The portions of the cavities 13 forming the rods 14 typically extend along a direction perpendicular to the outer face 12 of the molding strip 1. The portions of the cavities 13 forming the rods 14 have typically a geometry of rotation about an axis perpendicular to the outer face 12 of the molding strip 1, or a geometry having a plane of symmetry extending along a direction parallel to the direction of travel of the molding strip 1 and/or along a direction perpendicular to the direction of travel of the molding strip 1.

The portions of the cavities 13 forming the rods 14 have for example a generally frustoconical or cylindrical shape of rotation about an axis perpendicular to the outer face 12 of the molding strip 1, and having a rounding at the junction with the outer face 12 of the molding strip 1.

The portions of the cavities 13 forming the heads 15 typically extend radially or transversely relative to an axis perpendicular to the outer face 12 of the molding strip 1, and can have rotational symmetry about this axis perpendicular to the outer face 12 of the molding strip 1. The portions of the cavities 13 forming the heads 15 typically have a frustoconical or hexahedral, or substantially frustoconical or hexahedral shape.

The portions of the cavities 13 forming the heads 15 can be linear or curved, for example form portions curved towards the inner face 11 or towards the outer face 12 of the molding strip 1 extending from the portions of the cavities 13 forming the rods 14.

The portions of the cavities 13 forming the heads 15 can have a constant or variable thickness.

In the example represented in the figures, the portions of the cavities 13 forming the heads 15 extend radially around the portions of the cavities 13 forming the rods 14, and have the general shape of a disk, as can be seen in particular in FIG. 2 which will be presented subsequently.

The molding strip 1 can have on its inner face 11 or on its outer face 12 a particular texturing such as slots, network of grooves or network of passages forming vents or studs, or be smooth or substantially smooth.

The molding strip 1 can be formed by superposition of several strips, and is therefore not necessarily single-piece or single-material.

The molding strip can have, in the cross direction CD, a width comprised between 5 and 3,000 mm.

The molding device comprising a molding strip which has just been described is an example of a molding device. Other types of devices could be provided, for example of the type comprising plates provided with molding cavities, these plates being for example able to travel step by step.

It is also possible to provide another type of a molding device, for example of the type comprising rolls in which the molding cavities are directly produced.

They may be solid rolls, machined to present the molding cavities, or disks stacked to form a roll, the molding cavities being formed by machining of the edges of the disks and/or by cutting of the edges of the disks, for example by laser or water jet or by electrical discharge machining, particularly wire electrical discharge machining. Of course, the disks can be stacked by alternating solid disks with the perfectly circular or cylindrical edges, with disks whose edges have cutouts.

FIG. 2 represents the molding material once injected into the molding strip 1.

FIG. 2 represents a (sectional) side view of the material in the cavities 13 of the molding strip 1.

As seen in FIG. 2, the molding material penetrates into the molding strip so as to fill the cavity 13, thus forming a blank of retainer elements, in this case a rod and head blank for hooked retainer elements.

A layer of molding material is also deposited on the outer face 12 of the molding strip 1 so as to form a base for the retainer device, the thickness of this layer of molding material being determined by the air gap e between the outlet of the applicator 3 and the molding strip 1.

The air gap e typically has a thickness of less than 700 micrometers, or typically between 5 and 500 micrometers, or between 8 and 100 micrometers.

In the example represented, the cavities 13 of the molding strip 1 are through cavities. The equipment can then comprise an element such as a scraper 4 positioned so as to scrape the inner face 11 of the molding strip 1 to remove the excess molding material if necessary.

The injection of a molding material into the molding strip 1 by the applicator 3 therefore allows forming retainer elements in the cavities 13, the assembly thus forming a tape 100. These may be finished retainer elements or preforms which will then be subjected to a forming or calendering step for their finalization, as mentioned in the patent application WO2017187097. By "injection" it is meant here the action of shaping a molding material through the molten path, for example, the distribution, the supply, the molding, the injection, the extrusion.

The applicator 3 will now be described with reference to FIGS. 3 and 4. This applicator is in this case an extrusion device which comprises at least two adjacent channels, separated by a partition. In the example represented, the applicator 3 comprises three aligned channels 3A, 3B and 3C, the channel 3B being located between the channels 3A and 3C, from which it is separated by partitions 3' and 3".

For example, the application width L0 of the applicator is comprised between 70% and 100% of the useful width LB of the strip 1. Here, the concept of "application width"

means the cross distance, measured along the direction CD, between the most distant edges of the application channels. It is thus measured between an outer lateral edge of the channel 3A and the opposite outer lateral edge of the channel 3C. The three channels 3A, 3B and 3C in this case have the same width L1, which is for example comprised between 1 and 60 mm, in some cases between 2 mm and 50 mm, particularly between 3 mm and 30 mm. This width L1 is measured at the outlet of the channels. The partitions 3' and 3" in this case have the same width L2, also measured on the outlet face of the applicator, which is for example comprised between 0.5 mm and 15 mm, particularly between 0.5 mm and 10 mm. Preferably, the width L2 is smaller than or equal to the width L1.

The outlets of the channels 3A, 3B, 3C in this case have the form of rectangular openings of width L1 and height e1. The ratio e1/L1 is generally less than or equal to 2, or less than or equal to 1, even, as in the example represented, less than or equal to 0.5.

The outlets of the channels could have different shapes, for example by being square, circular, oval, elliptical or in the shape of a dog's bone, that is to say a generally rectangular shape, but with the bulging tips by forming one or two lobes.

In FIG. 4, the channels 3A, 3B and 3C are represented in schematic section taken in the plane IV-IV of progress of the molding material, while the molding strip is represented in external view according to the arrow IV. It can be seen that, at the outlet of the channels, three separate molding material flows 3A, 3B and 3C are formed. These three flows therefore apply the molding material to the surface 12 of the strip 1 in three application zones ZA, ZB and ZC, which are the zones of the surface located in line with the outlets of the channels, in the direction of progress of the molding material in the channels, which corresponds to the direction MD.

The application of the molding material leaving the channels forms tapes of molding material.

It can be seen that at the outlet of the channels and/or once applied on the surface 12, the molding material flows laterally (in the direction CD). Indeed, once applied on the strip 1, the material naturally tends to spread laterally to fill the space between two adjacent application zones. Due to the small width L2 of the partitions, the adjacent flows will naturally tend to meet. Thus, the zones of the strip 1 located in line with the partitions 3' and 3" form junction zones ZJ, ZJ' in which, due to the lateral flow of the molding material, the molding material tapes applied at the outlet of the channels 3A, 3B and 3C tend to meet. As indicated in FIG. 4 by the references f, the phenomenon of lateral creeping can take effect at the outlet of the channels, in the air gap e, possibly before the molding material comes into contact with the surface 12.

The molding material directly applied in the application zones ZA, ZB and ZC, through its progress in the direction MD will naturally fill the cavities 13 present in these zones, under the effect of its velocity component and the outlet pressures of the channels, which are then exerted mainly perpendicularly to the plane of the surface 12. On the other hand, in the junction zones ZJ and ZJ", this pressure is partly dedicated to the lateral creeping and its velocity component is exerted naturally and mainly along the direction CD. Due to its lateral spreading, the molding material is less likely to fill the cavities present in the junction zones. Thus, the parts of the retainer device coming from these junction zones have retainer elements which are degraded compared to those of the parts coming from the application zones, whereas the cavities 13 of the junction zones and of the application zones are identical or similar.

This is what is seen in FIG. 5. This figure shows a retainer device comprising a base 51 and retainer elements 50 which extend from the upper face 511 of the base 51. In this case, the retainer device also comprises a substrate 60 on the side of the lower face 512 of the base 51.

The upper face 511 and a lower face 512 of the base are typically parallel or substantially parallel, the upper face 511 being the face provided with the retainer elements 50.

It can be seen that the device has retainer zones RA, RB and RC, in which the retainer elements are standard. This means that the retainer elements present in these retainer zones have been generally correctly molded into the cavities.

The retainer elements of these zones all have substantially the same height h measured between the upper face 511 of the base 51 and their opposite upper end. This means in particular that the heights of these retainer elements are all between 80% and 100%, or between 85% and 100% and even 90% and 100% of the maximum height observed for these retainer elements.

Here, the geometric dimension taken into account is the height of the retainer elements. Other geometric dimensions could be taken into account, for example the thickness of the rods of the retainer elements measured in a plane parallel to the upper face of the base, or between the width of the heads of the retainer elements (if these are provided with heads), also measured in a plane parallel to the upper face of the base.

Between the retainer zones RA, RB and RC, the retainer device has intermediate zones RJ and RJ'. It can be seen that, among the retainer elements 50, the retainer elements 50A which are present in the intermediate zones RJ and RJ' are degraded compared to the other ones. Particularly, it is seen that their heights h' are lower than the height of the retainer elements present in the retainer zones and even, possibly, that these heights vary quite considerably from one retainer element 50A to another. It is even seen, in particular in FIG. 7 that the retainer elements 50A of the intermediate zones RJ and RJ' can be devoid of a head, unlike those of the retainer zones RA, RB and RC.

Here again, the height is only one of the geometric dimensions of the retainer elements 50A, which is taken into consideration to assess their degradation compared to the retainer elements present in the retainer zones. It is therefore understood here that the difference in shape between the retainer elements 50 of the retainer zones and of the intermediate zones results not from different geometries of the cavities 13 of the strip 1, but from a non-uniform filling of these cavities with the molding material between the application zones and the junction zones.

FIG. 6 shows the shape of elongated tapes along the direction MD presented by the retainer zones RA, RB and RC, the intermediate zones RJ and RJ' also having the form of generally less wide tapes (the width being measured in the direction CD). These intermediate zones have weld lines L and L', corresponding to the junction of the flows coming from the channels 3A and 3B on the one hand, and 3B and 3C on the other hand. In the intermediate zones, the base can have a state of material different from the one presented in the retainer zones. Particularly, the base can have a molecular orientation in the retainer zones which is homogeneous and for example along the direction MD, whereas the molecular orientation can vary in the intermediate zones, due to the creeping of the molding material in directions having a non-zero component along the direction CD.

It can however be seen that these different zones form the same common tape R, the intermediate zones forming the junction between the retainer zones.

As best seen in FIG. 6, the retainer elements 50 are distributed in a regular and repeating pattern. Here, they are disposed in rows parallel to the direction CD and columns parallel to the direction MD, the retainer elements of the adjacent rows and columns being disposed in a staggered manner.

It can also be seen in FIG. 4 that the cavities of the molding device are distributed in this regular and repeating pattern.

In FIGS. 5 and 7, it can be seen that, considering an intermediate zone RJ in the direction going from a retainer zone RA to the adjacent retainer zone RB, particularly a direction along the direction CD, the height of the retainer elements decreases towards a central zone of the intermediate zone, then increases.

The base 51 typically has a thickness eb comprised between 3 and 500 micrometers, or more specifically between 4 and 150 micrometers, or between 4 and 120 micrometers, or between 4.5 and 108 micrometers.

In the retainer zones RA, RB and RC, the thickness of the base is constant or substantially constant. It is measured between two adjacent retainer elements 50 of the retainer zones. By "substantially constant", it is meant that the thickness varies at most by 20%, even 10%, relative to an average value.

On the other hand, the thickness of the base 51 can be reduced in the intermediate zones RJ and RJ', as can be seen in FIGS. 5 and 7. It can for example decrease to represent 80%, or 60%, even 50% or less of the average thickness of the base in the retainer zones.

As can be seen in FIG. 8, it may even happen that the intermediate zone(s) RJ, RJ' have voids 50B. This corresponds to zones in which either the junction by creeping between the two zones of application of the molding material has not locally taken place, or the material has insufficiently penetrated into the cavities of the molding strip and has formed duct-shaped portions of retainer elements, or the material has penetrated into a cavity to form a degraded retainer element 50A, to the detriment of its lateral creeping, thus leaving a void at the foot of this degraded retainer element. The voids 50B generally have small dimensions. Particularly, the maximum dimension of a void, by the length of a segment going from one edge of the void to the other, parallel to the upper surface of the base, can be smaller than the minimum distance between two retainer elements.

The base 51 typically has a width comprised between 1 and 3,000 millimeters, or more specifically between 2 and 400 millimeters, or between 3 and 100 millimeters, the width of the base 51 being measured along the cross direction relative to the longitudinal direction, for example along a direction parallel to the outer face 12 of the molding strip 1. This width corresponds to the width called useful width LB of the strip 1 of the molding device.

Some geometric characteristics of a non-degraded retainer element 50 (that is to say present in a retainer zone) are described with reference to FIG. 9. This retainer element in this case has the shape of a hook, with a rod 52 and a head 53, which protrudes laterally from the rod. The total height h of the retainer element 50 can be of the order of 80 to 1,000 micrometers, particularly 90 to 500 micrometers, particularly 90 to 450 micrometers. The height h1 of the rod 52, measured from the upper face of the base 51 to the lower face of the head 53, can be of the order of 80 to 800 micrometers, particularly 90 to 450 micrometers or 90 to 300 micrometers. The height h2 of the head 53, measured between its lower and upper faces, between two planes parallel to the upper face of the base and tangent to said lower and upper faces, can be of the order of 5 to 200 micrometers, particularly 10 to 100 micrometers.

As indicated, the assembly formed by the base and the retainer elements can have a basis weight comprised between 10 and 120 $g/m^2$, particularly between 30 and 80 $g/m^2$, more particularly between 50 and 70 $g/m^2$.

The base itself can have a basis weight comprised between 5 and 80 $g/m^2$, particularly between 10 and 60 $g/m^2$.

The following ratios can be observed in the retainer zones:

rod height to base height: 0.8 to 80, particularly 1.5 to 65;

head height to base height: 0.1 to 30, particularly 0.3 to 22;

height of the rod/basis weight of the assembly formed by the base and the retainer elements: 1 to 10 (in micrometers/$g/m^2$).

The height of the retainer element is measured by the length of a line segment starting from the center of the retainer element, at the level of the upper surface of the base (average level of this surface verified between two adjacent retainer elements in the zone concerned) and reaching its point of intersection with the external envelope of the hook.

The base can be formed of a single material which can also be that of the retainer elements.

The demolding of the retainer device is typically carried out when the base is at a temperature lower than the melting temperature of the molding material, or lower than the temperature of deflection under load of the molding material, for example when the inner face 11 of the molding strip 1 is at a temperature of the order of 45° C. and the upper face 511 of the base 51 is at a temperature of the order of 75° C. The deflection temperature under load is commonly referred to as Heat Deflection Temperature or HDT.

The molding strip 1 is conventionally maintained, in the molding zone, at a temperature comprised between HDT− 30° C. and HDT+10° C., particularly between 50° C. and 120° C., particularly of the order of 80° C., particularly when the molding material is polypropylene or, in general, an ethylene copolymer. Since the base 51 can be extremely thin, the temperature of the molding strip, in the molding zone, can be slightly higher than HDT because the external surface of the base (opposite to the strip), which is in contact with the air is at a lower temperature than that of the strip and, due to the low thickness of the base, the internal face of the base and the retainer elements cool down as soon as the base separates from the molding strip.

The demolding step can be followed by a forming step, in which the second preforms are modified in particular at the level of their head 53.

As indicated, the retainer device can comprise a substrate 60. This substrate is typically a layer of non-woven material, a plastic film, an elastic film or a composite film, or a set of thermally consolidated fibers and/or filaments. The substrate 60 is for example a web of fibers and/or filaments.

By "non-woven" it is meant a product obtained at the end of the formation of a web of fibers and/or filaments that have been consolidated. The consolidation can be mechanical, chemical or thermal and results in the presence of a bond between the fibers and/or the filaments. This consolidation can be direct, that is to say made directly between the fibers and/or filaments by welding, or it can be indirect, that is to say via an intermediate layer between the fibers and/or the filaments, for example a glue layer or a binder layer. The term "non-woven" relates to a tape-shaped structure or web of fibers and/or filaments that are interleaved in a non-uniform, irregular or random manner. A non-woven material can have a single layer structure or a multilayer structure. A non-woven material can also be joined to another material to form a laminate. A non-woven material can be made from various synthetic and/or natural materials. The exemplary natural materials are cellulose fibers, such as cotton, jute, linen and the like and can also include re-treated cellulose fibers, such as rayon or viscose. The natural fibers for a non-woven material can be prepared by using various methods such as carding. Exemplary synthetic materials include, but are not limited to, synthetic thermoplastic polymers, which are known to form fibers that include, but are not limited to, polyolefins, for example, polyethylene, polypropylene, polybutylene and the like; polyamide, for example polyamide 6, polyamide 6.6, polyamide 10, polyamide 12 and the like; polyesters, for example polyethylene teraphthalates, polybutylene terephthalates, polylactic acids and the like, polycarbonates, polystyrenes, thermoplastic elastomers, vinyl polymers, polyurethanes and mixtures and co-polymers thereof. By way of example, the non-woven material can be a non-woven material of the Spunbond, Spunmelt, heat-bonded carded, SMS, SMMS, SS, SSS, SSMMS, SSMMMS, Air through type or the like.

The substrate is not limited to a non-woven material, and can more generally be a non-woven material, a woven material, a knitted material or a combination of several of these materials.

In the case where the substrate 60 is a non-woven material, it can be activated prior to its securing to the base. The substrate can comprise several distinct layers, in particular a support layer, which can itself be a non-woven material and possibly be activated.

By "plastic material" it is meant a thermoplastic material, more particularly a homopolymer or copolymer-based polyolefin material.

The materials mentioned in document WO2017187097 can be used to form the base and the retainer elements and, if present, the substrate. The substrate can be added onto the base as mentioned in document WO2017187097.

The object of the present disclosure allows, while having excellent retainer properties, possibly over substantial widths, ensuring that the retainer device is particularly light. In addition, it is very flexible, particularly in the intermediate zone(s). It constitutes a whole, the retainer zones being contiguous with the intermediate zone(s).

FIG. 10 shows an absorbent item 200 of the baby diaper or adult incontinence diaper type. Typically, the item 200 comprises an assembly which comprises two external sheets 210, 220 and an absorbent core 230 disposed between the external sheets. The item has a first face of the diaper (front face) FA, and sides of the diaper CC. The item comprises a hook-and-loop retainer system comprising receiving loops carried by one of the elements among the first face of the diaper FA and one of the sides of the diaper CC. In this case, in FIG. 10, the rectangle 240 materialized on the first face of the diaper FA comprises such receiving loops and corresponds to a comfort strip (generally designated by landing zone).

The item also comprises a retainer device 5 according to the present disclosure. In this case, such a device 5 is disposed on each of the sides CC so as to be able to cooperate with the receiving loops 240 which are here carried by the front face FA, in order to keep the item worn by the user closed.

The invention claimed is:

1. A retainer device, comprising:
a base extending along a longitudinal direction and having an upper face and a lower face,
a plurality of retainer elements extending from the upper face of the base, each retainer element having a value according to a first geometric dimension,
wherein:
the retainer device has at least two retainer zones and an intermediate zone disposed between the at least two retainer zones and connecting the at least two retainer zones, the retainer elements disposed in first and second retainer zones of the at least two retainer zones, the first and second retainer zones having values according to the first geometric dimension which are greater than the values according to the first geometric dimension of the retainer elements disposed in the intermediate zone, wherein the base and the retainer elements are made of a same material, wherein, the retainer elements of the at least two retainer zones are spaced apart from each other, and at least in the retainer zones, the retainer elements are each formed of a rod surmounted by a head protruding from the rod; wherein, considered in the direction going from the first retainer zone to the second retainer zone, the intermediate zone has successive retainer elements whose value according to the first geometric dimension decreases then retainer elements whose value according to the first geometric dimension increases.

2. The retainer device according to claim 1, wherein the retainer zones and the intermediate zone form elongated zones in the same tape.

3. The retainer device according to claim 1, wherein the intermediate zone has at least one part in which the base has a thickness smaller than a thickness of the base in the retainer zones.

4. The retainer device according to claim 1, wherein, in the intermediate zone, the base has voids.

5. The retainer device according to claim 1, wherein, in the retainer zones, the retainer elements have a value according to the first geometric dimension which is substantially constant.

6. The retainer device according to claim 1, wherein any straight line passing through at least one retainer element and extending along the direction going from the first retainer zone to the second retainer zone while passing through said first and second retainer zones, intersects at least 3 retainer elements in each of the first and second retainer zones.

7. The retainer device according to claim 1, wherein the first geometric dimension is the height of the retainer elements, measured, for each retainer element, between a lower end of the retainer element connected to the base and an upper end of the retainer element opposite to the lower end.

8. The retainer device according to claim 1, wherein an assembly formed by the base and the retainer elements has a basis weight comprised between 10 and 120 $g/m^2$.

9. The retainer device according to claim 1, further comprising a substrate carrying the base.

10. An absorbent item of the baby diaper or adult incontinence diaper type, the item comprising an assembly which comprises two external sheets and an absorbent core disposed between the external sheets, the assembly being arranged so as to present a first face of the diaper, and sides of the diaper, the item comprising a hook-and-loop retainer system comprising receiving loops carried by one of the elements among the first face of the diaper and one of the sides of the diaper, and at least one retainer device according to claim 1, carried by the other of the elements among the first face of the diaper and said one of the sides of the diaper, so that the retainer elements cooperate with the receiving loops when said at least one of the sides of the diaper is placed against the first face of the diaper to retain said at least one of the sides of the diaper with respect to said first face.

11. A method for manufacturing a retainer device, wherein:

a molding device is provided having a plurality of cavities formed in a recessed manner from a surface, a heated molding material is applied on said surface, using an applicator by allowing the molding material to penetrate into the cavities to form retainer elements, and characterized in that are generated two separate adjacent flows of a molding material applied on the surface in two application zones by causing the same molding material to flow so that the two flows meet in a junction zone so as to form a base, so that the material penetrates further into the cavities present in the application zones than into the cavities present in the junction zone for forming at least one retainer device according to claim 1.

12. The method according to claim 11, wherein the applicator is an extrusion device comprising two adjacent channels separated by a partition, and the molding material is applied by moving the molding device and the extrusion device relative to each other in a longitudinal direction.

13. The method according to claim 11, wherein, before cooling of the molding material, a substrate is applied against a plastic material applied on the surface of the molding device, so that said material is sandwiched between the surface of the molding device and the substrate.

14. The retainer device according to claim 1, wherein the retainer zones and the intermediate zone form elongated zones in the same tape, the elongated zones and the tape being elongated along the longitudinal direction.

15. The retainer device according to claim 1, wherein any straight line passing through at least one retainer element and extending along the direction going from the first retainer zone to the second retainer zone while passing through said first and second retainer zones, intersects at least 5 retainer elements in each of the first and second retainer zones and at least 1 retainer element in the intermediate zone.

16. The retainer device according to claim 1, wherein, at least in the retainer zones, the retainer elements are each formed of a rod surmounted by a head protruding from the rod, at least part of the retainer elements of the intermediate zone being devoid of a head.

17. The retainer device according to claim 1, wherein the assembly formed by the base and the retainer elements has a basis weight comprised between 30 and 80 g/m$^2$.

18. The retainer device according to claim 1, further comprising a substrate carrying the base, the substrate comprising a layer of non-woven material.

19. The retainer device according to claim 1, wherein the intermediate zone connects the at least two retainer zones contiguously, and the plurality of retainer elements are distributed in a regular and repeating pattern across the at least two retainer zones and the intermediate zone.

* * * * *